United States Patent [19]

Khanna et al.

[11] Patent Number: 5,300,396
[45] Date of Patent: Apr. 5, 1994

[54] PROCESS OF MAKING NAPHTHOQUINONE DIAZIDE ESTERS USING LACTONE SOLVENTS

[75] Inventors: Dinesh N. Khanna; Robert E. Potvin, both of Kent, R.I.

[73] Assignee: Hoechst Celanese Corporation, Somerville, N.J.

[21] Appl. No.: 619,154

[22] Filed: Nov. 28, 1990

[51] Int. Cl.$^5$ .............................. G03F 7/022
[52] U.S. Cl. .................... 430/169; 430/193
[58] Field of Search .............. 430/169, 190, 193

[56] References Cited

U.S. PATENT DOCUMENTS 4,929,536  5/1990  Spak et al. .................. 430/193
4,957,846  9/1990  Jeffries et al. ................ 430/190
5,080,997  1/1992  Hioki et al. .................. 430/169

Primary Examiner—Charles L. Bowers, Jr.
Assistant Examiner—Christopher G. Young
Attorney, Agent, or Firm—Andrew F. Sayko, Jr.

[57] ABSTRACT

A method of preparing a photosensitizer condensate comprising: condensing a phenolic compound with a diazo sulfonyl chloride, wherein from about 50 to 100 mole percent of the diazo moiety is 2,1,4-diazo and from 0 to about 50 mole percent of the diazo moiety is 2,1,5 diazo; the phenolic compound having, on average, from about 60 mole percent to about 100 mole percent of its hydroxy groups esterified by the diazo sulfonyl chloride; wherein the condensing is conducted in a lactone solvent in the presence of an acid scavenger; and then subsequently isolating the photosensitizer condensate.

8 Claims, No Drawings

PROCESS OF MAKING NAPHTHOQUINONE DIAZIDE ESTERS USING LACTONE SOLVENTS

FIELD OF THE INVENTION

The present invention relates to a method for producing naphthoquinone diazide esters of phenolic compounds using lactones as the solvent for the reaction mixture.

BACKGROUND OF THE INVENTION

It is well known in the art to produce positive photoresist formulations such as those described in U.S. Pat. Nos. 3,666,473, 4,115,128, 4,173,470 and 4,550,069. These include alkali-soluble novolak resins together with light-sensitive materials, usually a substituted naphthoquinone diazide compound. The resins and sensitizers are dissolved in an organic solvent or mixture of solvents and are applied as a thin film or coating to a substrate suitable for the particular application desired.

The novolak or polyvinyl phenol resin component of these photoresist formulations is soluble in aqueous alkaline solutions, but the naphthoquinone sensitizer acts as a dissolution rate inhibitor with respect to the resin. Upon exposure of selected areas of the coated substrate to actinic radiation, however, the sensitizer undergoes a radiation induced structural transformation and the exposed areas of the coating are rendered more soluble than the unexposed areas. This difference in solubility rates causes the exposed areas of the photoresist coating to be dissolved when the substrate is immersed in alkaline developing solution while the unexposed areas are largely unaffected, thus producing a positive relief pattern on the substrate.

An important group of photosensitizers are the condensation products of 1,2-naphthoquinonediazide-4-sulfonic acid or 1,2-naphthoquinonediazide-4-sulfonic acid and polyols. These compounds tend to exhibit superior photospeed and contrast in the mid-UV region of the light spectrum when formulated in photoresist compositions.

The trend in microlithography during the past few years has been an accelerated drive towards smaller geometries. The efforts to achieve these shrinking design rules require intensive efforts by both exposure tool and photoresist manufacturers. Therefore there is an increasing demand for UV-2 (DEEP-UV) and UV-3 (I-LINE) sensitive photoresist systems. Novolak containing photoresists are still workable for g-line and i-line type resists. 2,1,5-diazonaphthoquinone sulfonate esters of trihydroxy benzophenones are generally used as photoactive compounds (PAC) for broad band or g-line resists. On the other hand 2,1,4-diazonaphthoquinone esters are more suitable for i-line (365 nm) region.

Synthesis of such diazonaphthoquinone esters is normally conducted in a solvent system such as: N-methyl pyrollidone (NMP), acetone, acetonitrile or mixed solvent system. A base is generally used as a catalyst and also as an acid acceptor. Common organic bases used, while not inclusive, include pyridine, triethylamine, N-methyl morpholine, dimethyl amino pyridine and mixture thereof. The processes utilizing these solvent/base systems provide diazonaphthoquinone esters of consistently good quality. However, providing similar quality and consistency of the diazo esters becomes extremely difficult if a similar process is utilized for making 2,1,4-diazo esters or 2,1,4/2,1,5 mixed diazo esters. In addition, making 2,1,4 diazo esters or 2,1,4/2,1,5 mixed diazo esters becomes even more difficult when utilizing a tetrahydroxybenzophenone.

SUMMARY OF THE INVENTION

The invention relates to an improved process for making a diazonaphthoquinone sulfonate ester from a diazo sulfonyl chloride and a phenolic compound. More particularly, the invention relates to a process for making 2,1,4 and 2,1,5-diazo esters and mixed 2,1,4/2,1,5 diazo esters of phenolic compounds, such as benzophenones. The process utilizes a lactone as the reaction solvent and a base which serves as an acid scavenger such as; N-methyl morpholine (NMM). The preferred solvent is gamma-butyrolactone, which is a safe solvent for making such diazonaphthoquinone esters, is biodegradable and does not require any special safety and health precautions.

The subject process provides consistent quality diazonaphthoquinone esters, where the degree of esterification can be reproduced from batch to batch. The degree of esterification is extremely important in controlling batch to batch photospeed and resolution characteristics. In addition, the degree of esterification can be tailored by carefully controlling the stoichiometric amount of the diazo sulfonyl chloride. Examples 1 to 9 demonstrate the synthesis of diazo naphthoquinone esters, having varying degrees of esterification. The degree of esterification is established using HPLC techniques.

The process of the present invention can provide diazonaphthoquinone esters with no substantial amount of complex side products. These side products preclude the production of consistently yellow, substantially pure diazonaphthoquinone esters, in comparison to the gray, dark amber to even green color of impure diazo esters. The subject process can be easily controlled and a slight shift in reaction temperature, time, base concentration etc. does not lead to poor quality or inconsistent material.

The process of the present invention also allows washing, cleaning and drying of the diazo using ambient conditions. As low as 0.3 to 0.5% retained solvent (e.g. gamma-butyrolactone) can be achieved by drying the finished product in a vacuum oven at 40°-45° C. for 24-48 hrs. Higher amounts of retained solvent could be detrimental to obtaining consistent photospeed for the photoresist formulations. The process is cost effective, safe and leads to consistently high quality yellow colored diazo ester material and is applicable for a wide variety of diazo ester compositions.

The photosensitizer compositions may be obtained by condensing phenolic compounds with a diazo organic acid halides. The diazo and the organic acid halide may be condensed either sequentially or concurrently with a phenolic compounds to provide the diazo organic acid halide.

The diazo organic acid halide may be reacted preferably in stoichiometric quantities with the hydroxyl-bearing phenolic compounds. However, the phenolic compounds need not be completely esterified and less than stoichiometric quantities of the diazo and organic acid halide compounds may be condensed with the phenolic compounds. The total amount of diazo and organic acid halide reacted with the phenolic compounds should be sufficient to produce a photosensitizer composition capable of inhibiting the dissolution rate of an alkali-soluble resin.

The phenolic compounds which may be condensed with the diazo organic acid halide are represented by the general formulae (A), (B) and (C):

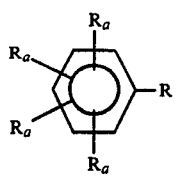 (A)

wherein R is —H, —OH, —X—R$_b$, or

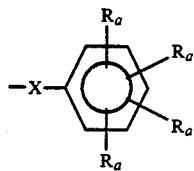 (A)

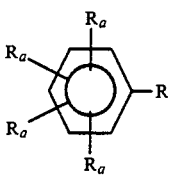

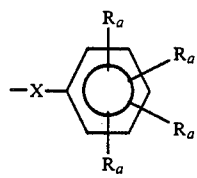

R$_a$ is H, —OH, halogen, preferably Cl or Br, or lower alkyl, preferably lower alkyl having 1 to 4 carbon atoms; with at least two and not greater than six R$_a$ radicals being —OH, X is a single C—C bond, —O—, —S—, —SO$_2$—,

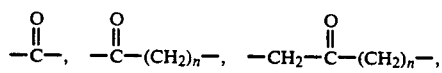

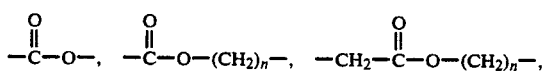

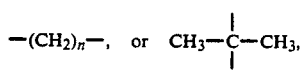

n is 1 or 2, R$_b$ is H, alkyl, aryl, substituted alkyl or substituted aryl; preferably alkyl having 1 to 20 carbon atoms, more preferably 1 to 12 carbon atoms, preferably aryl being phenyl or naphthyl, alkyl or aryl may be substituted with lower alkyl having 1 to 4 carbon atoms, lower alkoxy having 1 to 4 carbon atoms, or halogen atoms, preferably Cl or Br;

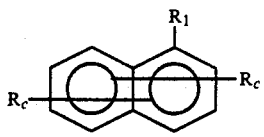 (B)

wherein R$_1$ is H or

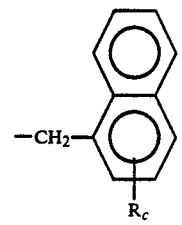

R$_c$ is H or —OH with at least two R$_c$ radicals being —OH; and

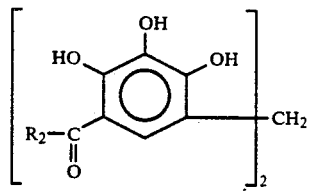 (C)

wherein R$_2$ is H, alkyl, aryl, substituted alkyl, or substituted aryl; the alkyl radicals R$_2$ may be straight-chain or branched and may be substituted with halogen atoms or lower alkoxy groups having 1 to 4 carbon atoms, preferably the alkyl radicals have 1 to 20 carbon atoms; the aryl radicals R$_2$ are preferably mononuclear and may be substituted with lower alkyl or alkoxy groups having 1 to 4 carbon atoms or with halogen atoms, preferably the aryl radicals have 1 to 10 carbon atoms; compounds in which R$_2$ is an aryl radical are particularly preferred and compounds in which the aryl radical is a phenyl radical are especially preferred.

Among the phenolic compounds represented by the general formula (A) are: hydroxyl-bearing benzene compounds such as 1,2-dihydroxybenzene, 1,3-dihydroxybenzene, 1,4-dihydroxybenzene, 1,2,3-trihydroxybenzene, 1,2,4-trihydroxybenzene, 1,3,5-trihydroxybenzene, and the like; dihydroxybenzophenones such as 2,2'-dihydroxybenzophenone, 2,3'-dihydroxybenzophenone, 2,4-dihydroxybenzophenone, 2,4'-dihydroxybenzophenone, 2,5-dihydroxybenzophenone, 3,3'-dihydroxybenzophenone, 4,4'-dihydroxybenzophenone, and the like; trihydroxybenzophenones such as 2,2',6-trihydroxybenzophenone, 2,3,4-trihydroxybenzophenone, 2,4,4'-trihydroxybenzophenone, 2,4,6-trihydroxybenzophenone, 3,4,5-trihydroxybenzophenone, and the like; tetrahydroxybenzophenones such as 2,2'3,4-tetrahydroxybenzophenone, 2,2',4,4'-tetrahydroxybenzophenone, 2,2'4,6'-tetrahydroxybenzophenone, 2,2',5,6'-tetrahydroxybenzophenone, 2,3',4,4'-tetrahydroxybenzophenone, 2,3,6,4'-tetra hydroxy benzophenone, 2,3',4,6-tetrahydroxybenzophenone, 2,4,4',6-tetrahydroxybenzophenone, 3,3',4,4',-tetrahydroxybenzophenone, and the like; pentahydroxybenzophenones; hexahydroxybenzophenones; dihydroxy- and trihydroxy- phenyl alkyl ketones such as 2,4-dihydroxyphenyl alkyl ketones, 2,5-dihydroxyphenyl alkyl ketones, 3,4-dihydroxyphenyl alkyl ketones, 3,5-dihydroxyphenyl alkyl ketones, 2,3,4-trihydroxyphenyl alkyl ketones, 3,4,5-trihydroxyphenyl alkyl ketones, 2,4,6-trihydroxyphenyl alkyl ketones, and the like, preferably alkyl having 1 to 12 carbon atoms such as methyl, ethyl, butyl, n-hexyl, heptyl, decyl, dodecyl, and the like; dihydroxyphenyl aralkyl ketones; trihydroxyphenyl aralkyl ketones; dihydroxydiphenyls; trihydroxydiphenyls such as 2,2',4-trihydroxydiphenyl; tetrahdroxydiphenyls such as 2,2',4,4'-tetrahydroxydiphenyl; dihydroxydiphenyl oxides; dihydroxydibenzyl oxides; dihydroxydiphenyl alkanes, preferably lower alkanes such as methane, ethane, propane or the like; dihydroxybenzoic acid; trihydroxybenzoic acids; dihydroxy- and trihydroxy- benzoic acid alkyl esters, alkyl preferably having 1 to 12 carbon atoms, such as n-butyl 2,4-, 2,5-, 3,4- and 3,5-dihydroxybenzoate, 2,4,4-trimethylpentyl 2,4-dihydroxybenzoate, and the like; dihydroxy- and trihydroxy- benzoic acid phenyl esters; dihydroxy-, trihydroxy-, and tetrahydroxy- diphenyl sulfides such as 4,4'dihydroxydiphenyl sulfide; dihydroxydiphenyl sulfones; and dihydroxy- and trihydroxy- phenyl naphthyl ketones such as 2,3,4-trihydroxyphenyl naphthyl ketones; and the like.

Examples of compounds of general formula (A) where at least one $R_a$ radical is halogen or lower alkyl include 2,4-dihydroxy-3,5-dibromobenzophenone; 5-bromo-2,4-dihydroxybenzoic acid and esters; 2,4,2',4'-tetrahydroxy-3,5,3',5'-tetrabromodiphenyl; 4,4'-dihydroxy-2,2'dimethyl-5,5'-di-tert.-butyl diphenyl; 4,4'-dihydroxy-2,2'dimethyl-5,5'-di-tert.-butyl diphenyl sulfide; 2,4,2',4'-tetrahydroxy-3,5,3',5'-tetrabromodiphenyl sulfone; and the like.

The preferred class of phenolic compounds of general formula (A) are the hydroxyl-bearing benzophenones and the especially preferred compounds are the tetrahydroxybenzophenones.

Among the phenolic compounds represented by general formula (B) are: dihydroxynaphthalenes such as 1,2-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,6-dihydroxynaphthalene, 2,7-dihydroxynaphthalene, and the like; dihydroxydinaphthylmethanes such as 2,2'dihydroxydinaphthylmethane, and the like. The dihydroxynaphthylenes are preferred. The hydroxyl groups of the dihydroxynaphthylenes may be either on the same nucleus or on different nucleii of the naphthalene moiety.

Among the phenolic compounds represented by general formula (C) are bis-(3-benzoyl-4,5,6-trihydroxyphenyl)-methane; bis-(3-acetyl-4,5,6-trihydroxyphenyl)-methane; bis-(3-propionyl-4,5,6-trihydroxyphenyl)-methane; bis-(3-butyryl-4,5,6-trihydroxyphenyl)-methane; bis-(3-hexanoyl-4,5,6-trihydroxyphenyl)-methane; bis-(3-heptanoyl-4,5,6-trihydroxyphenyl)-methane; bis-(3-decanoyl-4,5,6-trihydroxyphenyl)-methane; bis-(3-octadecanoyl-4,5,6-trihydroxyphenyl)-methane; and the like.

Among the organic acid halides which may be reacted with a 1,2-naphthoquinone-5-sulfonic acid or 1,2-naphthoquinone-4-sulfonic acid to produce the 2,1,4- and 2,1,5-diazonaphthoquinone sulfonyl chlorides utilized in the process of the present invention are: alkyl sulfonyl halides such as methanesulfonyl chloride, ethanesulfonyl chloride, propanesulfonyl chloride, n-butanesulfonyl chloride, dodecanesulfonyl chloride, and the like; arylsulfonyl chlorides such as benzenesulfonyl chloride, naphthalenesulfonyl chlorides, and the like; acyl halides such as acetyl chloride, butanoyl chloride, valeryl chloride, benzoyl chloride, benzoyl bromide, naphthoyl chlorides, and the like. The preferred organic acid halides are lower alkyl sulfonyl halides having 1 to 6 carbon atoms, benzenesulfonyl halides and benzoyl halides. The acid halides may be substituted or unsubstituted.

The acid scavenger may be inorganic, such as sodium carbonate or the like, or organic amines such as triethyl amine, pyridines or N-methyl morpholine.

According to the present invention there is provided a method of preparing a photosensitizer condensate comprising: condensing a phenolic compound represented by the general formulae (A):

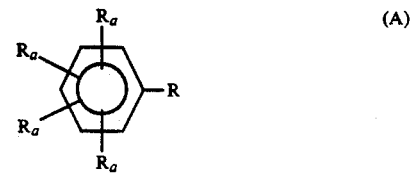

wherein R is

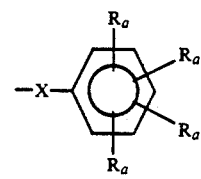

$R_a$ is H, —OH, halogen lower or lower alkyl, with at least two and not greater than six $R_a$ radicals being —OH, X is a single C—C bond, —O—, —S—, —SO$_2$—,

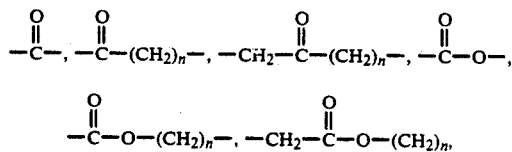

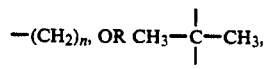

n is 1 or 2; with a diazo sulfonyl chloride, wherein from about 50 or 100 mole percent of the diazo moiety is 2,1,4-diazo and from 0 to about 50 mole percent of the diazo moiety is 2,1,5 diazo; the phenolic compound having, on average, from about 60 mole percent to about 100 mole percent of its hydroxy groups esterified by the diazo sulfonyl chloride; the condensation reaction is conducted in a lactone solvent preferably selected from the group consisting of gamma-butyrolactone, gamma-valerolactone and delta-valerolactone which may be mixed with another solvent such as acetonitrile, normally used in the production of naphthoquinone diazide esters used as photosensitizers in the presence of an acid scavenger; and then subsequently isolating the photosensitizer condensate.

The following specific examples will provide detailed illustrations of the method of the present invention. These examples are not intended to limit or restrict the scope of the invention in any way and should not be construed as providing conditions, parameters or values which must be utilized exclusively in order to practice the present invention. Examples 1-9 illustrate the process of the present invention. Comparative examples 10-12 illustrate similar processes utilizing solvents other than those of the present invention.

EXAMPLE 1

Synthesis of 2,1,4 Diazo Ester of 2,3,4,4' Tetrahydroxy Benzophenone, 88% Stoichiometry Into a one liter four necked flask equipped with a thermometer, stirring shaft and dropping funnel were added 12.3 grams (0.05 moles) of 2,3,4,4' tetrahydroxy benzophenone and 47.256 grams (0.176 moles) of 2,1,4-diazo sulfonyl chloride and 300 ml. of gamma-butyrolactone. The mixture was stirred at room temperature (25° C.) for about 10 minutes to obtain a clear solution.

A separate solution was prepared by dissolving 20.23 grams of N-methyl morpholine (0.2 moles) in 20 ml. of gamma-butyrolactone in a dropping funnel. The solution was added into the reaction flask over 30 minutes maintaining temperature at 20° C. The reaction mixture was stirred for 2 hours at room temperature. After the reaction was complete, 4.0 ml. of glacial acetic acid was added to destroy any unreacted sulfonyl chloride. The reaction mixture was stirred for one hour and then filtered to remove salt and any impurities.

The reaction mixture was precipitated by drowning into 4 liters of deionized water. A yellow fine precipitate was obtained which was stirred for several hours then decanted and filtered and washed with about 4 liters of distilled water. The yellow cake was air dried first at room temperature by drawing air through a Buchner funnel. After the cake was air dried it was placed in a vacuum oven at 40°-50° C. overnight. The yield of the product was 51.7 grams.

HPLC data indicate ester distribution to be: 41.22% Tetraester, 49.29% Triester, 8-9% Di/Tri esters and traces of unreacted materials.

EXAMPLE 2

Synthesis of 2,1,4 Diazo Ester of 2,3,4,4' Tetrahydroxy Benzophenone, 100% Stoichiometry, 1:4 (Tetra hydroxy benzophenone:2,1,4 Diazo Sulfonyl Chloride)

Into a three liter four necked flask equipped with a thermometer, stirring shaft and dropping funnel were added 49.2 grams (0.20 moles) of 2,3,4,4' tetrahydroxy benzophenone and 213.8 grams (0.80 moles) of 2,1,4-diazo sulfonyl chloride and 1200 ml. of gamma-butyrolactone. The mixture was stirred at room temperature (25° C.) for about 10 minutes to obtain a clear solution.

A separate solution was prepared by dissolving 89.2 grams of N-methyl morpholine (0.88 mole) in 80 ml. of gamma-butyrolactone into a dropping funnel. The solution was added into the reaction flask over 30 minutes maintaining temperature at 20° C. The reaction mixture was stirred for 4 hours at room temperature. After the reaction was complete, 4.0 ml. of glacial acetic acid was added to destroy any unreacted sulfonyl chloride. At this stage 12.5 grams (5%) of Amberlyst-15 was added, stirred overnight and filtered to remove any metallic impurities and salts formed during the reaction. The recovered Amberlyst and reaction salts were rinsed with 200 ml. of gamma-butyrolactone.

The reaction mixture was precipitated by drowning into 12 liters of deionized water/1200 ml. methanol. A fine yellow precipitate was obtained which was stirred for several hours then decanted and filtered and washed with about 16 liters of distilled water. The yellow cake was air dried first at room temperature by drawing air through a Buchner funnel. After the cake was air dried, it was placed in a vacuum oven at 40°-50° C. overnight. The yield of the product was 225 grams.

HPLC data indicate ester distribution to be: 92.3% Tetraester, 4.4% Triester, 2-3% mono/Di/Tri esters.

EXAMPLE 3

Synthesis of 2,1,4 Diazo Ester of 2,3,4,4' Tetrahydroxy Benzophenone, 95% Stoichiometry, 1:3.8 (Tetra hydroxy benzophenone:2,1,4, Diazo Sulfonyl Chloride, (Target ~ 80% Tetra Esters)

Into a three liter four necked flask equipped with a thermometer, stirring shaft and dropping funnel were added 49.2 grams (0.20 moles) of 2,3,4,4' tetrahydroxybenzophenone and 204.2 grams (0.76 moles) of 2,1,4-diazo sulfonyl chloride and 1200 ml. of gamma-butyrolactone. The mixture was stirred at room temperature (25° C.) for about 10 minutes to obtain a clear solution.

The temperature was decreased to 15° C. and 84.6 grams of N-methyl morpholine (NMM) was charged into a dropping funnel. The NMM solution was added into the reaction flask over 30 minutes maintaining temperature at 20° C. The reaction mixture was stirred for 3.5 hours at room temperature. After the reaction was complete, 10 ml. of glacial acetic acid was added and the reaction mixture was stirred for 1 hour. TLC shows no residual Diazo sulfonyl chloride at this stage.

The reaction mixture was precipitated by drowning into 10 liters of deionized water and 1200 ml. methanol. A fine yellow precipitate was obtained which was stirred for several hours then decanted and filtered and washed with about 16 liters of distilled water. The yellow cake was air dried first at room temperature by drawing air through a Buchner funnel. After the cake was air dried, it was placed in a vacuum oven at 40°-50° C. overnight. The yield of the product was 224.3 grams (yield=99.4%).

HPLC data indicate ester distribution to be: 81.2% Tetraester, 17.4% Triester, 1-2% mono/Di/Tri esters.

EXAMPLE 4

Synthesis of 2,1,4 diazo ester of 2,3,4,4' Tetrahydroxy Benzophenone 92.5% Stoichiometry. 1:3.7 (Tetra hydroxy:2,1,4 Diazo Sulfonyl Chloride), (Target ~ 70% Tetra Esters)

Into a three liter four necked flask equipped with a thermometer, stirring shaft and dropping funnel were added 49.2 grams (0.20 moles) of 2,3,4,4' tetrahydroxy benzophenone and 198.8 grams (0.74 moles) of 2,1,4-diazo sulfonyl chloride and 1200 ml. of gamma-butyrolactone. The mixture was stirred at room temperature (25° C.) for about 10 minutes to obtain a clear solution.

The temperature was decreased to 15° C. and 82.3 grams of N-methyl morpholine (NMM) was charged into the dropping funnel. The NMM solution was added into the reaction flask over 30 minutes maintaining temperature at 20° C. The reaction mixture was stirred for 3.5 hrs. at room temperature. After the reaction was complete 10 ml. of glacial acetic acid was added and the reaction mixture was stirred for 1 hour. TLC shows no residual diazo sulfonyl chloride at this stage.

The reaction mixture was precipitated by drowning into 10 liters of deionized water and 1200 ml. methanol. A fine yellow precipitate was obtained which was stirred for several hours then decanted and filtered and washed with about 16 liters of distilled water. The yellow cake was air dried first at room temperature by drawing air through a Buchner funnel. After the cake was air dried it was placed in a vacuum oven at 40°-50° C. for overnight. The yield of the product is 221.1 grams (yield=98.5%).

HPLC data indicate ester distribution to be: 71.4% Tetra, 26.8% Triester, 1-2% mono/Di/Tri esters.

EXAMPLE 5

Synthesis of mixed (2,1,4 and 2,1,5/90:10) Diazo Esters of 2,3,4,4' Tetrahydroxy Benzophenone, 100% Stoichiometry, 1:40 Tetra hydroxy:2,1,4/2,1,5 [90:10] Diazo Sulfonyl Chloride Into a one liter four necked flask equipped with a thermometer, stirring shaft and dropping funnel were added 12.3 grams (0.05 moles) of 2,3,4,4' tetrahydroxy benzophenone and 48.33 grams (0.18 moles) of 2,1,4-diazo sulfonyl chloride, 5.37 grams (0.02 moles) of 2,1,5 diazo sulfonyl chloride and 400 ml. of gamma-butyrolactone. The mixture was stirred at room temperature (25° C.) for about 10 minutes to obtain a clear solution.

The temperature was decreased to 15° C. and 22.3 grams of N-methyl morpholine (NMM) and 20 ml. gamma-butyrolactone was charged into the dropping funnel. The NMM solution was added into the reaction flask over 30 minutes maintaining the temperature at 20° C. The reaction mixture was stirred for 1.5 hrs. at room temperature. After the reaction was complete 6 ml. of glacial acetic acid was added and the reaction mixture was stirred for 1 hour. TLC shows no residual diazo sulfonyl chloride at this stage.

The reaction mixture was precipitated by drowning into 2.5 liters of deionized water and 250 ml. methanol. A fine yellow precipitate was obtained which was stirred for several hours then decanted and filtered and washed with about 4 liters of deionized water. The yellow cake was air dried first at room temperature by drawing air through a Buchner funnel. After the cake was air dried it was placed in a vacuum oven at 40°-50° C. for overnight. The yield of the product was 56.1 grams (yield=95.5%).

EXAMPLE 6

Synthesis of mixed (2,1,4 and 2,1,5/50:50) Diazo Esters of 2,3,4,4' Tetrahydroxy Benzophenone, 100% Stoichiometry, 1:40 Tetra hydroxy:2,1,4/2,1,5 [50:50] Diazo Sulfonyl Chloride Into a one liter four necked flask equipped with a thermometer, stirring shaft and dropping funnel were added 12.3 grams (0.05 moles) of 2,3,4,4' tetrahydroxy benzophenone and 26.8 grams (0.10 moles) of 2,1,4-diazo sulfonyl chloride, 26.8 grams (0.10 moles) of 2,1,5 diazo sulfonyl chloride and 400 ml. of gamma-butyrolactone. The mixture was stirred at room temperature (25° C.) for about 10 minutes to obtain a clear solution.

The temperature was decreased to 15° C. and 22.3 grams of N-methyl morpholine (NMM) and 20 ml. gamma-butyrolactone was charged into the dropping funnel. The NMM solution was added into the reaction flask over 30 minutes maintaining temperature at 20° C. The reaction mixture was stirred for 2.5 hrs. at room temperature. After the reaction was complete, 6 ml. of glacial acetic acid was added and the reaction mixture was stirred for 1 hour. TLC shows no residual diazo sulfonyl chloride at this stage.

The reaction mixture was precipitated by drowning into 2.5 liters of deionized water and 250 ml. methanol. A fine yellow precipitate was obtained which was stirred for several hours then decanted and filtered and washed with about 4 liters of deionized water. The yellow cake was air dried first at room temperature by drawing air through a Buchner funnel. When the cake was air dried it was placed in a vacuum oven at 40°-50° C. for overnight. The yield of the product was 55.9 grams (yield=95.0%).

COMPARATIVE EXAMPLE 7

Synthesis of 2,1,4 Diazo Ester of 2,3,4,4' Tetrahydroxy Benzophenone, 88% Stoichiometry, using acetonitrile as a solvent Into a one liter four necked flask equipped with a thermometer, stirring shaft and dropping funnel where added 12.3 grams (0.05 moles) of 2,3,4,4' tetrahydroxy benzophenone and 47.256 grams (0.176 moles) of 2,1,4-diazo sulfonyl chloride and 400 ml. of acetonitrile. The mixture was stirred at room temperature (25° C.) for about 10 minutes but a clear solution was not obtained.

A separate solution was prepared by dissolving 10.12 grams of triethylamine (0.1 mole), 11.20 grams of dimethylamino pyridine (0.1 mole) in 20 ml. of acetonitrile in a dropping funnel. The solution was added into the reaction flask over 30 minutes maintaining temperature at 20° C. The reaction mixture was stirred for 2 hours at room temperature and 4.0 ml. of glacial acetic acid was added to destroy any unreacted sulfonyl chloride in the reaction mixture, which was very dark. The reaction mixture was stirred for one hour and then filtered to remove salt and solid impurities.

The reaction mixture was precipitated by drowning into a mixture of 4 liters of deionized water and 400 ml. methanol. A fine dark gray precipitate was obtained which was stirred for several hours then decanted and filtered and washed with about 4 liters of distilled water. The dark gray cake was air dried first at room temperature by drawing air through a Buchner funnel. The dark gray color of the cake indicated that a significant amount of impurities were present. After the cake was air dried, it was placed in a vacuum oven at 40°-50° C. overnight. The material turned orange/yellow after drying in the vacuum oven.

COMPARATIVE EXAMPLE 8

Synthesis of 2,1,4 Diazo Ester of 2,3,4-trihydroxy benzophenone, 100% Stoichiometry, 1:4 (trihydroxy benzophenone: 2,1,4 Diazo Sulfonyl Chloride), using acetonitrile as a solvent Into a one liter four necked flask equipped with a thermometer, stirring shaft and dropping funnel were added 23.0 grams (0.10 mole) of 2,3,4-trihydroxy benzophenone and 88.67 grams (0.33 mole) of 2,1,4-diazo sulfonyl chloride and 345 ml. of acetonitrile. The mixture was stirred at room temperature (20° C.) for about 20 minutes to obtain a solution.

Over a period of about 20 minutes, 35 grams of N-methyl morpholine (0.346 mole) was added into the reaction flask while maintaining a temperature of about 20° C. 6.0 grams of additional N-methyl morpholine was added. The reaction mixture was stirred for one hour at a temperature of about 30° C. 12 grams of glacial acetic acid was rapidly added. The reaction mixture was stirred for 1½ hours while being gradually cooled to 13° C. The reaction mixture was then filtered.

The reaction mixture was precipitated by stirring in 115 ml. of methanol. A precipitate was obtained which was stirred for one hour at 13° C., then decanted and filtered and washed with about 460 ml. of methanol. The cake was air dried first at room temperature by drawing air through a Buchner funnel. After the cake was air dried it was placed in a vacuum oven at 35° C. overnight. The yield of the product was 86.0 grams (92.9% of theoretical). The lower yield and color bodies in the product indicated that a significant amount of impurities was produced.

COMPARATIVE EXAMPLE 9

Synthesis of 2,1,4 Diazo Ester of 2,3,4,4' Tetrahydroxy Benzophenone, using acetone as a solvent Into a one liter three necked flask equipped with a thermometer and stirring shaft were added 23.0 grams (0.10 mole) of 2,3,4,4' tetrahydroxybenzophenone and 84.6 grams (0.315 mole) of 2,1,4-diazo sulfonyl chloride, and 350 ml. of acetone. The mixture was stirred at a temperature of 25° C. for about 10 minutes to obtain a solution.

The temperature was increased to 30° C. and 36.4 grams of triethylamine was added. The reaction mixture was stirred for one hour at a temperature of 30° C. 12 grams of glacial acetic acid was added and the reaction mixture was stirred for 1½ hours. Darco and Celite filtration aids were added to 350 ml. of acetone.

The reaction mixture, which contained dark impurities, was washed with the acetone and filtered, then dropped into 3500 ml. of 1N hydrochloric acid. Colored specks were observed and the filtrate was colored. A precipitate was obtained which was stirred for several hours then decanted, filtered and washed with about 4 liters of deionized water. The cake was air dried first at room temperature by drawing air through a Buchner funnel. After the cake was air dried, it was placed in a vacuum oven at 40°-50° C. overnight. The yield of the product was 92.3 grams (yield=99.6%).

EXAMPLE 10

Synthesis of 2,1,4 Diazo Ester of 2,3,4,4' Tetrahydroxy Benzophenone Using Gamma-Butyrolactone Solvent and Dimethyl Amino Pyridine (DMAP) as Base, 1:4 (Tetra Hydroxy:2,1,4 Diazo Sulfonyl Chloride)

Into a one liter four necked flask equipped with a thermometer, stirring shaft and dropping funnel were added 4.9 grams (0.02 moles) of 2,3,4,4' Tetrahydroxy benzophenone and 21.5 grams (0.08 moles) of 2,1,4-diazo sulfonyl chloride and 120 ml. of gamma-Butyrolactone. The mixture was stirred at room temperature (25° C.) for about 10 minutes to obtain a clear solution.

A separate solution was prepared by dissolving 9.8 grams of (0.088 moles) dimethyl amino pyridine (DMAP) in 20 ml. of gamma-Butyrolactone into a dropping funnel. The solution was added into the reaction flask over 15 minutes maintaining temperature at 20° C. The reaction mixture was stirred for 4.5 hours at room temperature. After the reaction was complete, 2.0 ml. of glacial acetic acid was added to destroy any unreacted sulfonyl chloride. The reaction mixture was stirred for one hour and then filtered to remove salt and any impurities.

The reaction mixture was precipitated by drowning into 1 liter of deionized water and 120 ml. methanol. A fine precipitate was obtained which was stirred for several hours then decanted and filtered and washed with about 4 liters of distilled water. The yellow cake was air dried first at room temperature by drawing air through a Buchner funnel. After the cake was air dried, it was placed in a vacuum oven at 40°-50° C. for overnight. The yield of the product was 22.4 grams (96.6%).

HPLC data indicate ester distribution to be: 64.4% Tetra, 24.75% Triester, 10% Di/Tri esters and traces of unreacted materials.

EXAMPLE 11

Synthesis of 2,1,4 Diazo Ester of 2,3,4,4' Tetrahydroxy Benzophenone Using Gamma-Butyrolactone Solvent and Triethyl Amine as Base, 1:4 (Tetra Hydroxy:2,1,4 Diazo Sulfonyl Chloride)

Into a one liter four necked flask equipped with a thermometer, stirring shaft and dropping funnel were added 4.9 grams (0.02 moles) of 2,3,4,4' Tetrahydroxy benzophenone and 21.5 grams (0.08 moles) of 2,1,4-diazo sulfonyl chloride and 120 ml. of gamma-Butyrolactone. The mixture was stirred at room temperature (25° C.) for about 10 minutes to obtain a clear solution.

A separate solution was prepared by dissolving 8.9 grams (0.088 moles) of triethylamine in 20 ml. of gamma-Butyrolactone into a dropping funnel. The solution was added into the reaction flask over 15 minutes maintaining temperature at 20° C. The reaction mixture was stirred for 4.5 hours at room temperature. After the reaction was complete, 2.0 ml. of glacial acetic acid was added to destroy any unreacted sulfonyl chloride. The reaction mixture was stirred for one hour and then filtered to remove salt and any impurities.

The reaction mixture was precipitated by drowning into 1 liter of deionized water and 120 ml. methanol. A fine precipitate was obtained which was stirred for several hours then decanted and filtered and washed with about 4 liters of distilled water. The yellow cake was air dried first at room temperature by drawing air through a Buchner funnel. After the cake was air dried, it was placed in a vacuum oven at 40°-50° C. for overnight. The yield of the product was 22.6 grams (97.5%). A gray colored product was obtained.

HPLC data indicate ester distribution to be: 80.8% Tetra, 18.0-20.0% Di/Tri esters and traces of unreacted materials.

EXAMPLE 12

Synthesis of 2,1,4-Diazo Ester of 2,3,4,4'-Tetrahydroxy Benzophenone, 100% Stoichiometry, 1:4 (Tetrahydroxy:2,1,4-Diazo Sulfonyl Chloride), A Mixed Solvent System of 25% Acetonitrile and 75% Γ-Butyrolactone Into a 250 ml. flask were added 4.92 grams Tetrahydroxy benzophenone (0.02 mole), 21.50 grams 2,1,4-Diazo sulfonyl chloride (0.08 mole), 25 ml. Acetonitrile, and 75 ml. Γ-Butyrolactone and stirred. The mixture was cooled to 15° C. and 10.0 ml. of N-methylmorpholine was dropped in. The temperature was adjusted to 30° C. and an alkaline pH was maintained for 3 hours. To this mixture was added 1 ml water and 12 g Acetic acid. The mixture was allowed to stand overnight and was drowned into a solution mixture of 1 liter water and 200 ml. methanol. The precipitated product was filtered, washed with water and dried in an oven at 35°-40° C. The yield was 23.2 grams (99% of theory).

HPLC data show the ester distribution to be 92.5% tetraester and the remainder to be lesser esterified fractions.

GC results were Acetonitrile not detectible and Γ-Butyrolactone was 0.8%.

EXAMPLE 13

Synthesis of 2,1,4-Diazo Ester of 2,3,4,4'-Tetraydreoxy Benzophenone, 100% Stoichiometry, 1:4 (Tetrahydroxy:2,1,4-Diazo Sulfonyl Chloride), An Alternate Solvent, Γ-Valerolactone Into a 100 ml. flask were added 2.462 grams Tetrahydroxy benzophenone (0.01 mole), 10748 grams 2,1,4-Diazo sulfonyl chloride (0.04 mole), and 50 ml Γ-Valerolactone (Γ=gamma) and stirred. The mixture was cooled to 20° C. and 5.0 ml. of N-methylmorpholine was dropped in. The temperature was adjusted to 30° C. and an alkaline pH was maintained for 2 hours. To this mixture was added 1 ml. water and 6 grams Acetic acid. The mixture was allowed to stand overnight and was drowned into a solution mixture of 500 ml. water and 100 ml. methanol. The precipitated product was filtered, washed with water and dried in an oven at 35°-40° C. The yield was 12.0 grams.

HPLC data show the ester distribution to be 85.6% tetraester and the remainder to be lesser esterified fractions.

GC result was 4.2% Γ—Valerolactone retained.

EXAMPLE 14

Synthesis of 2,1,4-Diazo Ester of 2,3,4,4'-Tetrahydroxy Benzophenone, 100% Stoichiometry, 1:4 (Tetrahydroxy:2,1,4-Diazo Sulfonyl Chloride), An Alternate Solvent, δ-Valerolactone Into a 100 ml. flask were added 2.462 grams Tetrahydroxy benzophenone (0.01 mole), 10748 grams 2,1,4-Diazo sulfonyl chloride (0.04 mole), and 50 ml. δ-Valerolactone (δ=delta) and stirred. The mixture was cooled to 20° C. and 5.0 ml. of N-methylmorpholine was dropped in. The temperature was adjusted to 30° C. and an alkaline pH was maintained for 2 hours. To this mixture was added 1 ml. water and 6 grams Acetic acid. The mixture was allowed to stand overnight and was drowned into a solution mixture of 500 ml. water and 100 ml. methanol. The precipitated product was filtered, washed with water and dried in an oven at 35°-40° C. The yield was 11.9 grams.

HPLC data show the ester distribution to be 89.5% tetraester and the remainder to be lesser esterified fractions.

GC result was 1.4% δ—Valerolactone.

What is claimed is:

1. A method of preparing a photosensitizer condensate comprising: condensing a phenolic compound represented by the general formulae (A):

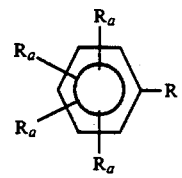

where in R is

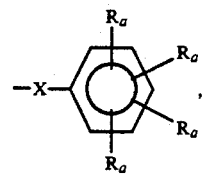

$R_a$ is H, —OH, halogen or lower alkyl, with at least two and not greater than six $R_a$ radicals being —OH, X is a single C—C bond, —O—, —S—, —SO$_2$—,

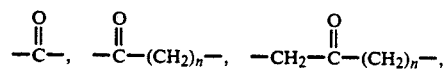

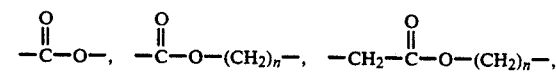

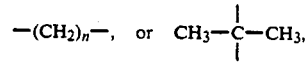

n is 1 or 2; with a diazo sulfonyl chloride, wherein from about 50 to 100 mole percent of the diazo moiety is 2,1,4-diazo and from 0 to about 50 mole percent of said diazo moiety is 2,1,5 diazo; said phenolic compound having, on average, from about 60 mole percent to about 100 mole percent of its hydroxy groups esterified by said diazo sulfonyl chloride; wherein said condensing is conducted in a lactone solvent in the presence of an acid scavenger; and then subsequently isolating said photosensitizer condensate.

2. The process of claim 1 wherein said solvent medium is selected from the group consisting of gamma-butyrolactone, gamma-valerolactone and delta-valerolactone.

3. The process of claim 1 wherein said lactone solvent is mixed with another solvent normally used as a solvent for the production of photosensitizers.

4. The process of claim 1 wherein said sulfonyl chloride comprises 2,1,4-diazo sulfonyl chloride and 2,1,5-diazo sulfonyl chloride.

5. The process of claim 1 wherein said sulfonyl chloride comprises 2,1,4-diazo sulfonyl chloride.

6. The process of claim 1 wherein said phenolic compound comprises a benzophenone.

7. The process of claim 6 wherein said benzophenone comprises 2,3,4,4'-tetrahydroxybenzophenone.

8. A method of preparing a photosensitizer condensate comprising: condensing a phenolic compound represented by the general formulae (A):

where in R is

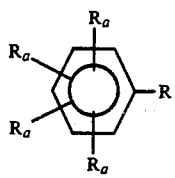

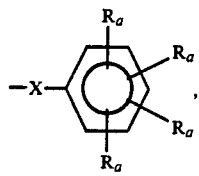

$R_a$ is H, —OH, halogen or lower alkyl, with at least two and not greater than six $R_a$ radicals being —OH, X is a single C—C bond, —O—, —S—, —SO$_2$—, $$-\overset{O}{\underset{\|}{C}}-, \quad -\overset{O}{\underset{\|}{C}}-(CH_2)_n-, \quad -CH_2-\overset{O}{\underset{\|}{C}}-(CH_2)_n-,$$

$$-\overset{O}{\underset{\|}{C}}-O-, \quad -\overset{O}{\underset{\|}{C}}-O-(CH_2)_n-, \quad -CH_2-\overset{O}{\underset{\|}{C}}-O-(CH_2)_n-,$$

$$-(CH_2)_n-, \quad \text{or} \quad CH_3-\underset{|}{\overset{|}{C}}-CH_3,$$

n is 1 or 2; with a diazo sulfonyl chloride, wherein from about 50 to 100 mole percent of the diazo moiety is 2,1,4-diazo and from 0 to about 50 mole percent of said diazo moiety is 2,1,5 diazo; said phenolic compound having, on average, from about 60 mole percent to about 100 mole percent of its hydroxy groups esterified by said diazo sulfonyl chloride; wherein said condensing is conducted in a gamma-butyrolactone solvent in the presence of an acid scavenger; and then subsequently isolating said photosensitizer condensate.

* * * * *